United States Patent
Ohkura et al.

(10) Patent No.: US 6,415,670 B1
(45) Date of Patent: Jul. 9, 2002

(54) INJECTION APPARATUS

(75) Inventors: Kihachiro Ohkura; Shigeo Mukai; Kunihiko Fujii, all of Osaka (JP)

(73) Assignee: Yamazen Corporation (JP)

( * ) Notice: Subject to any disclaimer, the term of this patent is extended or adjusted under 35 U.S.C. 154(b) by 0 days.

(21) Appl. No.: 09/534,989

(22) Filed: Mar. 27, 2000

(30) Foreign Application Priority Data

Mar. 26, 1999 (JP) .......................................... 11-084852

(51) Int. Cl.$^7$ ................................................ G01N 1/00
(52) U.S. Cl. .................. 73/864.83; 73/61.56
(58) Field of Search ...................... 73/61.55, 61.56, 73/61.57, 863.71, 863.72, 863.73, 863.81, 863.83, 864.83; 210/659, 198.2; 96/105; 436/180

(56) References Cited

U.S. PATENT DOCUMENTS

| | | | | |
|---|---|---|---|---|
| 3,230,048 A | * | 1/1966 | Skeggs | 23/253 |
| 3,373,872 A | * | 3/1968 | Hrdina | 210/198 |
| 3,827,303 A | * | 8/1974 | Shiina | 73/422 GC |
| 4,221,568 A | * | 9/1980 | Boettger | 23/230 |
| 4,991,428 A | * | 2/1991 | Heyde | 73/61.1 C |
| 5,283,036 A | * | 2/1994 | Hofmann et al. | 422/70 |
| 5,316,728 A | * | 5/1994 | Hayashi et al. | 422/70 |
| 5,660,792 A | * | 8/1997 | Koike | 422/63 |
| 5,695,720 A | * | 12/1997 | Wade et al. | 422/82 |
| 5,968,367 A | * | 10/1999 | Quinn et al. | 210/656 |
| 6,063,283 A | * | 5/2000 | Shirota et al. | 210/656 |
| 6,155,123 A | * | 12/2000 | Bakalyar | 73/864.83 |

FOREIGN PATENT DOCUMENTS

JP  1-41473  12/1989

* cited by examiner

Primary Examiner—Hezron Williams
Assistant Examiner—Charles D. Garber
(74) Attorney, Agent, or Firm—Connolly Bove Lodge & Hutz LLP

(57) ABSTRACT

An injection apparatus of the present invention includes a first switching valve RV1 which is selectively connected to any of a plurality of injectors 21–30 at one end sides thereof; a second switching valve RV2 which is selectively connected to any of the plurality of injectors at the other end sides thereof; a third switching valve RV4 which is connected to the second switching valve and is selectively connected to any of a plurality of columns 31–40 at one end sides thereof; and a fourth switching valve RV5 which is selectively connected to any of the plurality of columns at the other end sides thereof A sequential switching of these four switching valves can permit the sample liquids in the injectors 21–30 to be delivered in sequence into any selected column 31–40, and as such can allow the sample liquids packed in the plurality of injectors to be efficiently dispensed or analyzed by a chromatograph.

1 Claim, 4 Drawing Sheets

(a)

(b)

INJECTION APPARATUS

BACKGROUND OF THE INVENTION

1. Technical Field of the Invention

The present invention relates to an injection apparatus and, more particularly, to an sample injection apparatus for use in a liquid chromatograph that can perform preparative liquid chromatography with high efficiency.

2. Description of the Prior Art

In a liquid chromatograph using a liquid solvent (elution solvent) as a mobile phase, it is required that a sample liquid and a solvent be delivered in sequence into a column packed with a stationary phase, and an apparatus, which is called an injector, is generally used with the liquid chromatograph. However, injectors commonly used in the analytical liquid chromatographs are not suitable for a large quantity of sample injection required in a preparative liquid chromatography. Therefore, a sample liquid has to be injected directly into the column by opening the upper end of the column, which is very troublesome work.

An injector intended for easing such a troublesome work is known from the applicant's Japanese Utility Model Publication No. Hei 1(1989)-41473. The known injector has a cylinder including therein three plugs of a fixed plug, a floating plug, and a movable plug which are vertically arranged in order and having a ring-shaped recess in an inside wall thereof. According to this injector, as the floating plug rises, the sample liquid above the floating plug is delivered, while, when the floating plug is moved up to the recess, the solvent below the floating plug is delivered passing through clearances therebetween. This can provide the advantage that a large quantity of the sample liquid and the solvent can be delivered in sequence into the column without any troublesome work and with speed by use of only a single injector.

However, even in the use of the injector disclosed in the publication above, delivery of several kinds of sample liquids into the column for separation requires that a plurality of injectors packed with the sample liquid be each replaced in sequence with the next injector after each completion of the delivery of the sample liquid in each of the injectors. These works are of troublesome and it takes long time for the replacement. Thus, the prior art has a disadvantage that preparative chromatography of sample liquids cannot be done efficiently.

SUMMARY OF THE INVENTION

Accordingly, it is a primary object of the present invention to provide an injection apparatus for permitting preparative chromatography of the sample liquids packed in a plurality of injectors to be efficiently done.

An injection apparatus according to the present invention comprises a first switching valve which is selectively connected to any of a plurality of injectors at one end sides thereof; a second switching valve which is selectively connected to any of the plurality of injectors at the other end sides thereof; a third switching valve which is connected to the second switching valve and is selectively connected to any of a plurality of columns at one end sides thereof; and a fourth switching valve which is selectively connected to any of the plurality of columns at the other end sides thereof.

According to the injection apparatus of the present invention, since any of the plurality of injectors can be selectively connected between the first switching valve and the second switching valve, the switching of these two valves can permit any one of the plurality of injectors to be connected to the upstream side and the third switching valve. Also, since any of the plurality of columns can be selectively connected between the third switching valve and the fourth switching valve, the switching of these two valves can permit any one of the plurality of columns to be connected to the second switching valve and the downstream side. Accordingly, the sample liquids in the plurality of injectors can be delivered in sequence into any selected columns by the selective switching among the first to fourth switching valves.

Then, an automatic switching operation of the 1st to 4th switching valves will be permitted once the injectors and the columns are installed in the injection apparatus. This can provide a relatively simple work and also can save time for the replacement of the injectors and the columns. Thus, an efficient analysis and dispense can be achieved in a short time.

It should be noted that upon using the injection apparatus of the present invention, one injector and one column are not necessarily required to be associated with each other. In other words, it is not necessary to change the column every time the injector is replaced. One column may be brought into association with two or more injectors.

The injector known from the aforementioned JP Utility Model Publication No. Hei 1(1989)-41473 may be used as the injector in the present invention. In the present invention, two or more injectors are of sufficient, but actually, 5 to 15 injectors are of optimal in terms of readiness in handling and economics.

Preferably, the rotary valve disclosed by the applicant's JP Patent Laid-Open No. Hei 11(1999)-201955 is used as the switching valve. The rotary valve comprises a stator and a rotor which are allowed to rotate in contact with each other. The stator has one central through hole at the center thereof and a plurality of through holes on the circumference of a circle in the peripheral part thereof. The rotor has one aperture at the center thereof and one aperture in the peripheral part thereof. The both apertures are communicated with each other in the interior of the rotor or thereunder. The use of this rotary valve is of advantageous in that the fluidal contact area in the contact surface of the rotor and the stator can be reduced, as compared with the use of a general type of switching valve, and as such can retard occurrence of contamination.

It is preferable that in the injection apparatus of the present invention, at least one liquid sensor is provided between the second switching valve and the third switching valve. In this case, only when liquid is detected by one liquid sensor, the switching of the second switching valve and the third switching valve can be permitted to deliver the liquid in the injector to the associated column. This can permit the entry of almost no air into the columns, so the sample liquid can be separated adequately in the column. The use of only the single liquid sensor will have the difficulty in discharging out the air completely from the column in such cases that the liquid is delivered catching the air therein. Accordingly, two or more liquid sensors are of preferable.

Other and further objects, futures and advantages of the invention will appear more fully from the following description taken in connection with the accompanying drawings.

DESCRIPTION OF THE PREFERRED EMBODIMENT

In the following, an injection apparatus of one preferred embodiment of the invention will be described with reference to the accompanying drawings.

Figure 1:
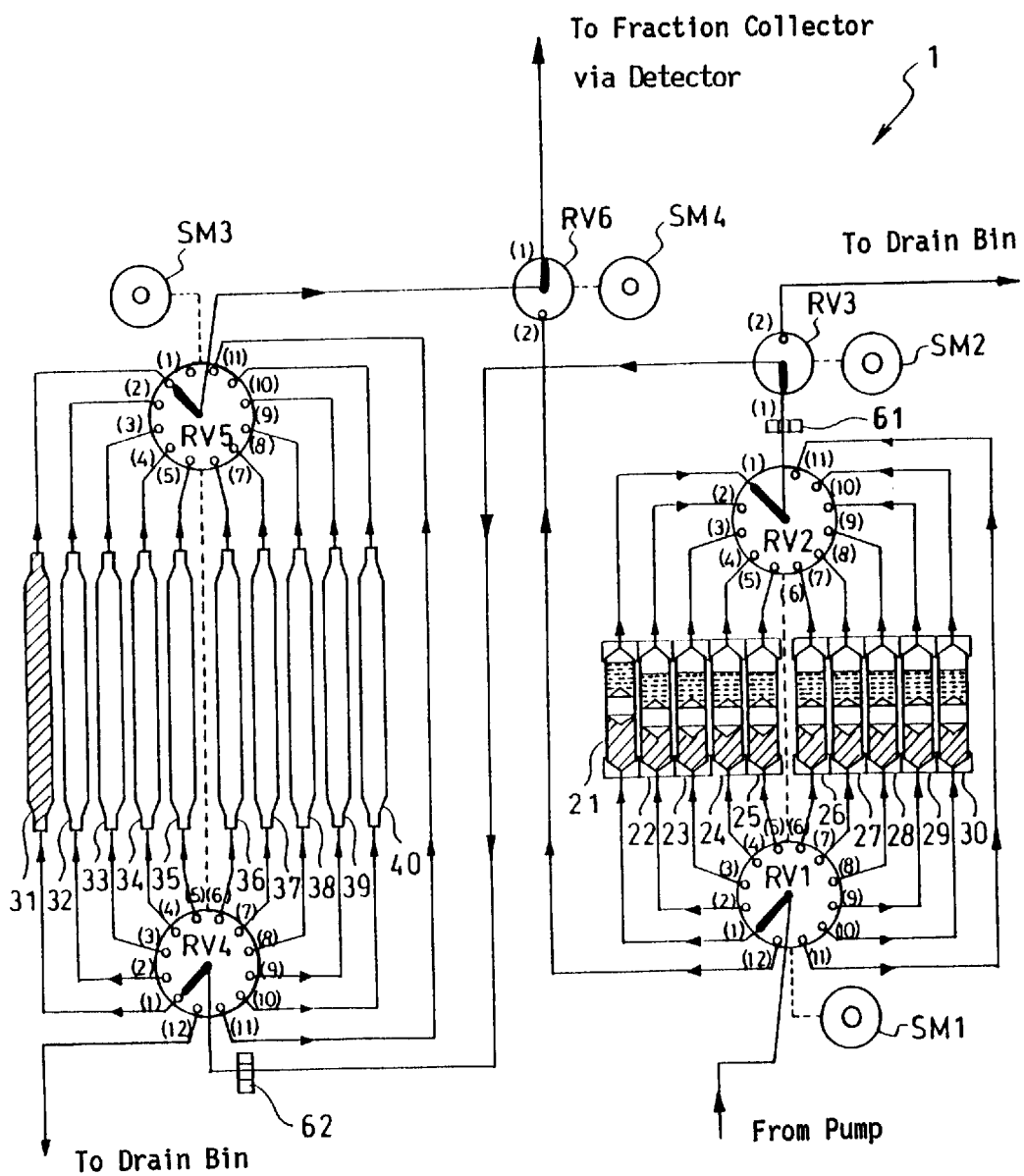
FIG. 1 is a schematic view of an injection apparatus of one embodied form of the invention in connection with injectors and columns.

Referring to FIG. 1, a diagrammatic, schematic view shows an injection apparatus of one embodied form of the invention in connection with injectors and columns. The injection apparatus 1 shown in FIG. 1 is provided with six rotary valves (switching valves) RV1–RV6.

Figure 2:
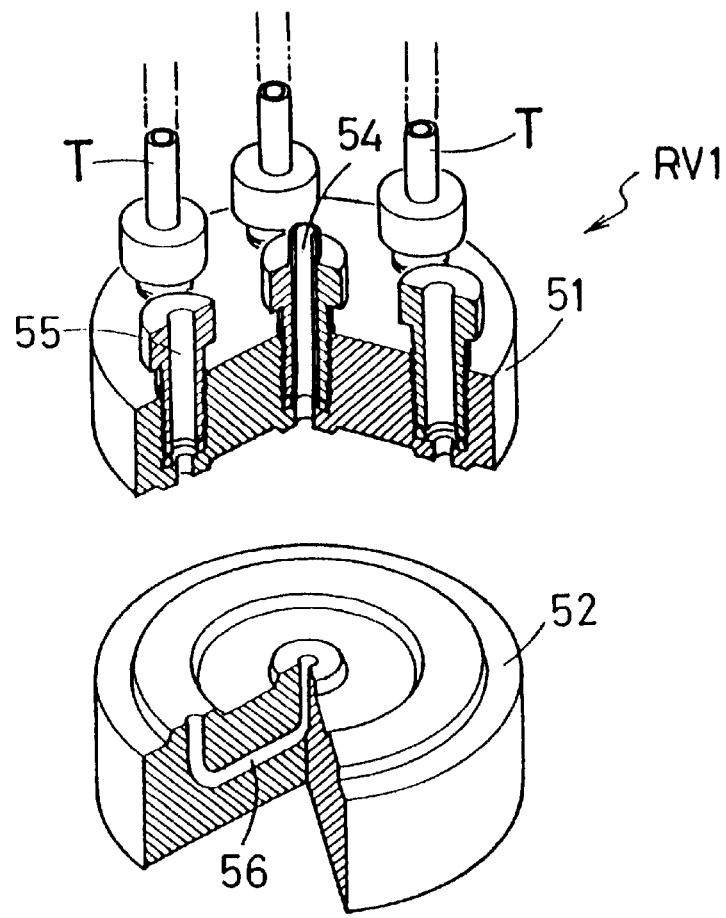
FIG. 2 is an exploded schematic view in perspective of a rotary valve, partially broken away, used in the injection apparatus of FIG. 1.
Figure 3:
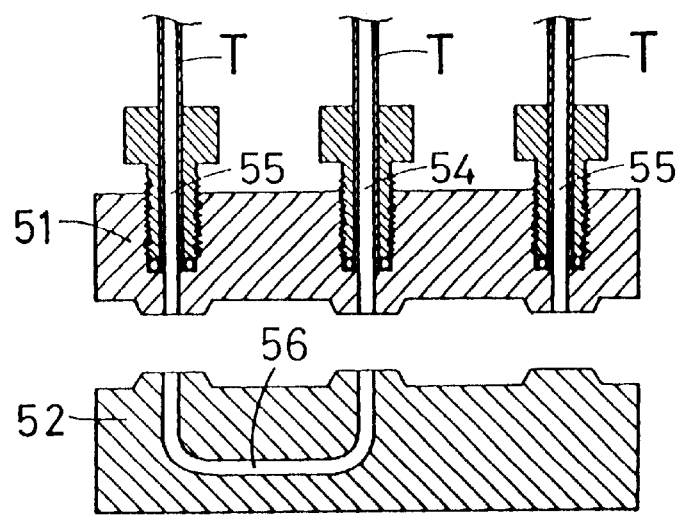
FIG. 3 is a schematic view in section of the rotary valve used in the injection apparatus of FIG. 1.

Each of the six rotary valves (switching valves) RV1–RV6 has a structure shown in FIGS. 2 and 3. In FIGS. 2 and 3, the rotary valve RV1 is shown as an example, the other rotary valves RV2–RV6 being identical in structure to the rotary valve RV1, except the number of peripheral through holes. Specifically, the rotary valves RV1, RV4 each have twelve peripheral through holes, the rotary valves RV2 and RV5 each having eleven peripheral through holes and the RV3 and RV6 each having two peripheral through holes. The rotary valve RV1 has the form of two cylindrical columns being superposed and is composed of a stator 51 of a fixed disc and a rotor 52 of a rotating disc. The stator 51 has one central through hole 54 in its center and a plurality of peripheral through holes 55 formed on the circumference of a circle in the peripheral part thereof (six through holes are just illustrated in FIG. 2, for simplicity, but actually twelve through holes are formed). Connecting pipes T are connected to the central through hole 54 and the peripheral through holes 55, respectively. The rotor 52 has, in its upper surface, two apertures, one of which is formed in the center thereof and the other of which is formed in the peripheral part thereof. These apertures are communicated with each other at each end of a communicating passage 56 extending in the interior of the rotor 52.

Thus, relative rotation between the stator 51 and the rotor 52 can permit the connection between the central through hole 54 and any one of the peripheral through holes 55 through the communicating passage 56. The peripheral through holes 55 move one after another and are each brought into communication with the central through hole 54 at each one-sixth turn (actually, at each one-twelfth turn) of the rotor 52. While the stator 51 and the rotor 52 are depicted as being separated from each other in FIGS. 2 and 3, the both are, of course, in contact with each other.

Opposed portions of the stator 51 and the rotor 52 (i.e., a lower portion of the stator 51 and an upper portion of the stator 52) are each formed of polytetrafluoroethylene so as to be of high resistance to chemical attach and of small frictional coefficient.

In the rotary valve RV1, the stator 51 and the rotor 52 are not formed to be flat in their opposed surfaces but are formed into a concave-convex ring-like form, as shown in FIG. 3. The stator 51 and the rotor 52 are brought into contact with each other in the zone depicted by dots in FIG. 4(a), to reduce the frictional resistance between the stator and the rotor during the rotation, as compared with the conventional type of rotary valves.

Figure 4:
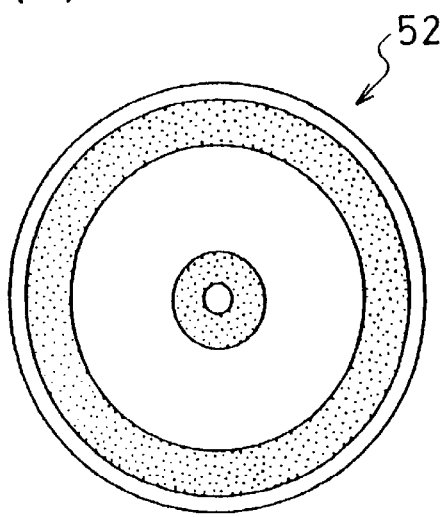
FIG. 4 is a schematic view in plan of a contacting part between a rotor and a stator of the rotary valve used in the injection apparatus of FIG. 1.
Figure 4:
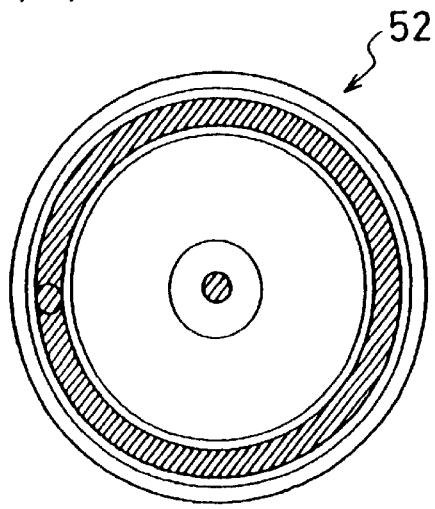

Shown in FIG. 4(b) is a fluidal contact zone of the rotary valve RV1 in the drive for rotation, which is the diagonally shaded area in the same figure. Thus, the rotary valve RV1 is designed to have a reduced fluidal contact zone, so as to considerably reduce a possible occurrence of contamination.

Figure 5:
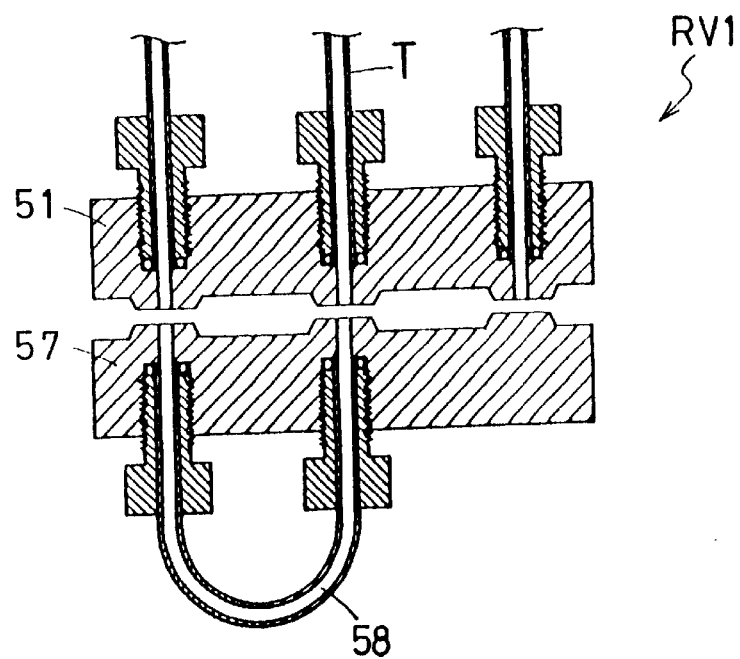
FIG. 5 is a schematic view in section of another rotary valve used in the injection apparatus of FIG. 1.

While the communicating passage 56 is formed in the interior of the rotor 52 in the illustrated example, in consideration of manufacturing difficulty due to the use of polytetrafluoroethylene of low moldability, modification may be made by forming two through holes in the rotor 57 and connecting those through holes by a U-like pipe 58, to form the communicating passage, as shown in FIG. 5.

The rotary valve RV1 thus constructed can produce the following advantages. Since the rotary valve has the reduced fluidal contact area, the residual liquid in the gap between the stator and the rotor is reduced and thus occurrence of contamination is retarded. Also, the reduced fluidal contact area of the rotary valve will reduce the frictional resistance in the drive for rotation, and as such can allow the driving power to decrease. Further, in the case of the communicating passage being formed by the U-like pipe, the manufacture of the rotary valve will be facilitated and also the communicating passage will have no sharp bend point, and as such can permit calm variation in the flow resistance to achieve a smooth flow of liquid in the delivery.

The rotary valve RV1 (1st switching valve) has the central through hole which is connected to a solvent mixer through a pump (both of which are not shown) and the twelve peripheral through holes, ten of which are connected to one end portions of the injectors 21–30, respectively. The remaining two peripheral through holes are connected to a peripheral through hole in the rotary valve RV2 and a peripheral through hole in the rotary valve RV6, respectively.

The rotary valve RV2 (2nd switching valve) has the central through hole which is connected to the central through hole in the rotary valve RV3 and eleven peripheral through holes, ten of which are connected to the other end portions of the injectors 21–30, respectively. The remaining one peripheral through hole is connected to the peripheral through hole of the rotary valve RV1.

The rotary valves RV1, RV2 are driven for rotation by a stepping motor SM1. The stepping motor SM1 is connected to a control unit of, for example, a personal computer through a drive circuit (not shown). Under the control of the stepping motor SM1 by the control unit, any desirable injector can be selected from among the injectors connected to the rotary valves RV1, RV2 at the opposite ends thereof.

The rotary valve RV3 has the central through hole connected to the central through hole of the rotary valve RV4. One of two peripheral through holes in the rotary valve RV3 is connected to the central through hole of the rotary valve RV2 and another is communicated to a drain bin. The rotary valve RV3 is driven for rotation by a stepping motor SM2 connected to the control unit through a drive circuit (not shown).

The rotary valve RV4 (3rd switching valve) has the central through hole which is connected to the central through hole in the rotary valve RV3 and twelve peripheral through holes, ten of which are connected to one end portions of columns 31–40, respectively. The remaining two peripheral through holes are connected to a peripheral through hole in the rotary valve RV5 and a drain bin, respectively.

The rotary valve RV5 (4th switching valve) has the central through hole which is connected to the central through hole in the rotary valve RV6 and eleven peripheral through holes, ten of which are connected to the other end portions of the columns 31–40, respectively. The remaining one peripheral through hole is connected to a peripheral through hole of the rotary valve RV4.

The rotary valves RV4, RV5 are driven for rotation by a stepping motor SM3. The stepping motor SM3 is connected to a control unit of, for example, a personal computer through a drive circuit (not shown). Under the control of the stepping motor SM3 by the control unit, any desirable column can be selected from among the columns connected to the rotary valves RV4, RV5 at the opposite ends thereof.

The rotary valve RV6 has the central through hole connected to the central through hole of the rotary valve RV5. One of two peripheral through holes in the rotary valve RV6 is connected to a peripheral through hole of the rotary valve RV1 and another is connected to a fraction collector by way of an ultraviolet detector. The rotary valve RV6 is driven for rotation by a stepping motor SM4 connected to the control unit through a drive circuit (not shown).

Next, description on the structure of the injectors 21–30 used for the illustrated injection apparatus will be given with reference to FIG. 6.

Figure 6:
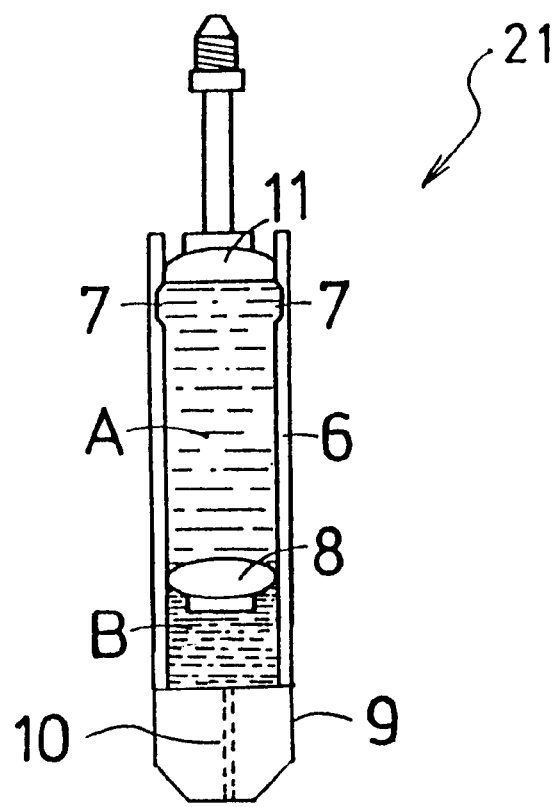
FIG. 6 is a schematic view of a structure of the injector used in the injection apparatus of FIG. 1.

Referring to FIG. 6, there is shown a schematic view a diagrammatic structure of the injector 21. The other injectors 22–30 are identical in structure to the injector 21. The injector 21 has a tubular cylinder 6 which is provided at its upper portion with a recess 7, at a central portion with a floating plug 8 and at a lower portion with a lower fixed plug 9. The recess 7 has a size of allowing the solvent to pass outside the floating plug 8 into above when the floating plug 8 just fits into the recess 7. The lower fixed plug 9 has at its center a through hole 10 which is communicated to a tube (not shown). The upper fixed plug 11 is fixed to the injector 21 after sample liquid A is charged in the injector 21 which is in the state of its upper portion opening to the air. The upper fixed plug 11 has at its center a through hole (not shown).

When solvent B is charged in the cylinder through the hole 10 of the lower fixed plug 9 under pressure, the floating plug 8 is forced to upwardly move. The floating plug 8 serves not only as a piston but also as a packing until it reaches the recess 7, to prevent the sample liquid A and the solvent B being mixed with each other. If the sample liquid A and the solvent B are mixed, then component characteristics analyzed in the columns will be SO broadened that the sample liquid cannot be separated adequately. This is why the floating plug 8 is provided.

When the floating plug 8 reaches the recess 7, a gap is formed between the floating plug 8 and the inner wall of the cylinder 6. From this stage forward, the solvent B is moved upwards above the floating plug 8 and is continuously discharged out from the injector 21.

The injector 21 thus structured enables the sample solution, the solvent and the like to be delivered without being mixed with each other by only a single injector, thus providing the advantage of doing the preparative liquid chromatography work for any quantity of the sample solution with high efficiency.

In the illustrated injection apparatus 1, the liquid sensors 61, 62 are provided between the rotary valves RV2 and RV3 and between the rotary valves RV3 and RV4, respectively. The liquid sensors 61, 62 detect the presence or absence of liquid in the pipes through the use of difference in index of refraction between liquid and air, for example.

The provision of these liquid sensors 61, 62 can prevent the entry of air into the columns 31–40. Thus, according to the illustrated injection apparatus 1, little deterioration occurs in the separating performances caused by the entry of air into the columns.

Next, the operation of the illustrated injection apparatus 1 will be described below. First, individual injectors are packed with one or two or more sample liquids to be analyzed and/or dispensed and in turn are connected to the injection apparatus 1. The illustrated injection apparatus is provided with ten injectors so that ten different kinds of sample liquids at maximum can be successively dispensed. A required number of columns can be connected to the injection apparatus 1. For example, if the individual columns are all used with one injector, ten columns will be connected to the injector.

The rotary valves RV1, RV2 are driven under the control of the stepping motor SM1, to connect the injector 21 with the part of the central through holes of the rotary valves RV1, RV2, and the rotary valves RV4, RV5 are driven under the control of the stepping motor SM3, to connect the column 31 with each of the central through holes of the rotary valves RV4, RV5. Further, under the control of the stepping motor SM2, the central through hole of the rotary valve RV3 is connected to the part of the central through hole of the rotary valve RV2, and under the control of the stepping motor SM4, the central through hole of the rotary valve RV6 is connected to the part of a detector.

In this condition, the solvent is charged from a pump, not shown, into the injector 21 through the rotary valve RV1. This forces the sample liquid 12 squeezed out from the injector 21 to be delivered to the column 31 through the rotary valves RV2, RV3, RV4. Then, after completion of the delivery of the sample liquid, the solvent in the injector 21 is delivered into the column 31 in the same manner. In the column 31, the sample liquid is separated into the components, which are delivered in sequence to the detector by way of the rotary valves RV5, RV6 and in turn are fractionated by the fraction collector. In this process, it is preferable to change the concentration of the solvent adequately, in order to increase the speed of the sample liquid passing through the column.

If air is detected by either of the liquid sensors 61, 62, the stepping motor SM3 is controlled to connect the central through hole of the rotary valve RV4 with the drain bit, so as to discharge out the air. Accordingly, the probability of the entry of air into the column 31 can be minimized.

After the completion of separation of the sample liquid packed in the injector 21, the rotary valves RV1–RV6 are switched for the washing of the passage and, if necessary, the column 31. At this time, the rotary valve RV1 is so controlled as to be connected with the rotary valve RV2 through neither of the injectors 21–30. Then, the separation of sample liquids in the injectors 22–30 can also be done in the same manner. In this separation process, either the same column or a different column may be used.

Thus, according to the illustrated injection apparatus 1, the sample liquids in the injectors 21–31 can be delivered in sequence into any selected columns by the selective switching of the rotary valves RV1–RV6. Accordingly, an automatic operation will be permitted once the injectors 21–30 and the columns 31–40 are installed in the injection apparatus 1. This can provide a relatively simple work and also can save time for the replacement of the injectors and the columns. Thus, an efficient analysis and preparative liquid chromatography can be permitted in a short time.

As mentioned above, according to the invention, the sample liquids in the plurality of injectors can be delivered in sequence into any selected column by the selective switching of the 1st to 4th switching valves. Then, an automatic operation will be permitted once the injectors and the columns are installed in the injection apparatus. This can provide a relatively simple work and also can save time for the replacement of the injectors and columns, thus permitting an efficient analysis and preparative liquid chromatography in a short time.

For example, even a variety of and a large quantity of sample liquids can be well analyzed by preparative liquid chromatography without being interrupted by the replacement of the injectors or other like works, because the injectors can be replaced one after another to permit the delivery of the liquids. Therefore, once operation starts, the operation can be effected without the assistance of an attendant, thus providing substantial labor savings.

While there has been described what are at present considered to be a preferred embodiment of the invention, it will be understood that various modifications may be made thereto, and it intended that the appended claims cover all such modifications as fall within the true spirit and scope of the invention.

What is claimed is:

1. An injection apparatus for preparative liquid chromatography comprising: a first switching valve one or more kinds of solvents to be supplied thereto, selectively connected to any of a plurality of injectors at one end thereof; each injector comprising a cylinder having a ring-shaped recess in the inside wall, two end plugs supported by the cylinder, and a floating plug movably inserted in the cylinder and positioned between the two end plugs, the floating plug isolating a sample liquid from the solvents in the cylinder before the floating plug reaches the recess; a second switching valve which is selectively connected to any of the plurality of injectors at the other end thereof; a third switching valve which is connected to the second switching valve and is selectively connected to any of a plurality of columns at one end thereof; and a fourth switching valve which is selectively connected to any of the plurality of columns at the other end thereof, a conduit connected between one port of the first switching valve and one port of the second switching valve; at least one liquid sensor is provided between the second switching valve and the third switching valve; wherein the valves are driven so that a selected column is connected to a selected injector only when liquid is continuously detected by all of the liquid sensor and the solvents are supplied to the selected column through the conduit after the sample liquid is sufficiently discharged from the selected injector.

* * * * *